United States Patent
Moloney et al.

(10) Patent No.: US 11,974,608 B2
(45) Date of Patent: May 7, 2024

(54) APPARATUS FOR GENERATING AEROSOL FROM AN AEROSOLIZABLE MEDIUM, AN ARTICLE OF AEROSOLIZABLE MEDIUM AND A METHOD OF OPERATING AN AEROSOL GENERATING APPARATUS

(71) Applicant: NICOVENTURES TRADING LIMITED, London (GB)

(72) Inventors: Patrick Moloney, London (GB); Anton Korus, London (GB); Justin Han Yang Chan, London (GB)

(73) Assignee: Nicoventures Trading Limited, London (GB)

( * ) Notice: Subject to any disclaimer, the term of this patent is extended or adjusted under 35 U.S.C. 154(b) by 800 days.

(21) Appl. No.: 15/733,696

(22) PCT Filed: Mar. 27, 2019

(86) PCT No.: PCT/EP2019/057784
§ 371 (c)(1),
(2) Date: Sep. 29, 2020

(87) PCT Pub. No.: WO2019/185749
PCT Pub. Date: Oct. 3, 2019

(65) Prior Publication Data
US 2021/0093011 A1    Apr. 1, 2021

(30) Foreign Application Priority Data
Mar. 29, 2018  (GB) ...................................... 1805268

(51) Int. Cl.
*A24F 40/50*    (2020.01)
*A24F 40/46*    (2020.01)
*A24F 40/51*    (2020.01)

(52) U.S. Cl.
CPC .............. *A24F 40/50* (2020.01); *A24F 40/46* (2020.01); *A24F 40/51* (2020.01)

(58) Field of Classification Search
CPC .......... A24F 40/53; A24F 40/40; A24F 40/50; A24F 40/60; A61M 11/042
(Continued)

(56) References Cited

U.S. PATENT DOCUMENTS

| | | |
|---|---|---|
| 5,082,365 A | 1/1992 | Kuzmick et al. |
| 5,388,594 A | 2/1995 | Counts et al. |

(Continued)

FOREIGN PATENT DOCUMENTS

| | | |
|---|---|---|
| CN | 102264251 A | 11/2011 |
| CN | 103932406 A | 7/2014 |

(Continued)

OTHER PUBLICATIONS

"International Preliminary Report on Patentability received for PCT Patent Application No. PCT/EP2019/057776, dated Jun. 26, 2020", 14 pages.

(Continued)

*Primary Examiner* — Gary F Paumen
(74) *Attorney, Agent, or Firm* — Burr & Forman, LLP

(57) ABSTRACT

A method of operating an aerosol generating apparatus is disclosed. The method includes sensing, at a first sensor of a sensor arrangement, a first indicia of an article including aerosolizable medium; sensing, at a second sensor of the sensor arrangement spaced a predetermined distance from the first sensor, a second indicia of the article; determining a distance between the first indicia and the second indicia; and operating the aerosol generating apparatus based at least on the distance between the first indicia and the second indicia.

18 Claims, 6 Drawing Sheets

(58) Field of Classification Search
USPC .................................................. 131/328, 329
See application file for complete search history.

(56) References Cited

U.S. PATENT DOCUMENTS

| | | | |
|---|---|---|---|
| 5,819,756 A | 10/1998 | Mielordt | |
| 6,053,176 A | 4/2000 | Adams et al. | |
| 7,331,339 B2* | 2/2008 | Smith | A61M 15/0085 |
| | | | 128/200.14 |
| 9,152,829 B2* | 10/2015 | Day | A61M 15/0083 |
| 9,769,878 B2* | 9/2017 | Xiang | A24F 40/53 |
| 10,076,137 B2* | 9/2018 | Krietzman | H05B 1/0244 |
| 2005/0172954 A1 | 8/2005 | Smith et al. | |
| 2006/0119835 A1 | 6/2006 | Rastegar et al. | |
| 2010/0163063 A1 | 7/2010 | Fernando et al. | |
| 2012/0101470 A1 | 4/2012 | Rasmussen et al. | |
| 2014/0309779 A1 | 10/2014 | Niu | |
| 2015/0189695 A1 | 7/2015 | Xiang | |
| 2016/0158782 A1 | 6/2016 | Henry et al. | |
| 2016/0331027 A1 | 11/2016 | Cameron | |
| 2016/0345627 A1 | 12/2016 | Liu | |
| 2017/0196269 A1 | 7/2017 | Bernauer et al. | |
| 2017/0259170 A1 | 9/2017 | Bowen et al. | |
| 2017/0266397 A1 | 9/2017 | Mayle et al. | |
| 2018/0043114 A1 | 2/2018 | Bowen et al. | |
| 2020/0093185 A1 | 3/2020 | Lim | |

FOREIGN PATENT DOCUMENTS

| | | |
|---|---|---|
| CN | 105806320 A | 7/2016 |
| CN | 106170215 A | 11/2016 |
| EP | 0893071 A1 | 1/1999 |
| EP | 1736053 A1 | 12/2006 |
| EP | 1736065 A1 | 12/2006 |
| EP | 2201850 A1 | 6/2010 |
| JP | H04271487 A | 9/1992 |
| JP | H07184627 A | 7/1995 |
| JP | H08130613 A | 5/1996 |
| JP | 2006215633 A | 8/2006 |
| JP | 2007507260 A | 3/2007 |
| JP | 2009289473 A | 12/2009 |
| JP | 2010020790 A | 1/2010 |
| JP | 2012513750 A | 6/2012 |
| JP | 2012517837 A | 8/2012 |
| JP | 2013534163 A | 9/2013 |
| JP | 2017501682 A | 1/2017 |
| JP | 2019521739 A | 8/2019 |
| JP | 2020513821 A | 5/2020 |
| KR | 20110096548 A | 8/2011 |
| RU | 2268631 C2 | 1/2006 |
| RU | 103281 U1 | 4/2011 |
| RU | 2604313 C2 | 12/2016 |
| RU | 2638514 C2 | 12/2017 |
| RU | 2646581 C2 | 3/2018 |
| TW | 138941 B | 8/1990 |
| WO | 9920132 A1 | 4/1999 |
| WO | 2007024130 A1 | 3/2007 |
| WO | 2007066374 A1 | 6/2007 |
| WO | 2007131449 A1 | 11/2007 |
| WO | 2007131450 A1 | 11/2007 |
| WO | 2010073122 A1 | 7/2010 |
| WO | 2011095870 A2 | 8/2011 |
| WO | 2014033439 A1 | 3/2014 |
| WO | 2014037794 A2 | 3/2014 |
| WO | 2015082560 A1 | 6/2015 |
| WO | 2015140312 A1 | 9/2015 |
| WO | 2016187695 A1 | 12/2016 |
| WO | 2017019428 A1 | 2/2017 |
| WO | 2017205692 A1 | 11/2017 |
| WO | 2021123321 A1 | 6/2021 |

OTHER PUBLICATIONS

"International Preliminary Report on Patentability received for PCT Patent Application No. PCT/EP2019/057783, dated Oct. 8, 2020", 8 pages.
"International Preliminary Report on Patentability received for PCT Patent Application No. PCT/EP2019/057784, dated Oct. 8, 2020", 9 pages.
"International Search Report and Written Opinion received for Patent Application No. PCT/EP2019/057776, dated Jul. 11, 2019", 15 pages.
"International Search Report and Written Opinion received for PCT Patent Application No. PCT/EP2019/057783, dated Jul. 23, 2019", 11 pages.
"International Search Report and Written Opinion received for PCT Patent Application No. PCT/EP2019/057784, dated Jul. 16, 2019", 12 pages.
"Notice of Allowance received for Korean Patent Application No. 10-2020-7028019, dated Apr. 7, 2023", 4 pages (1 page of English Translation and 3 pages of Official Copy).
"Office Action and Search Report received for Chinese Application No. 2019800228818, dated Jan. 9, 2023", 17 pages (8 pages of English Translation and 9 pages of Official Copy).
"Office Action and Search Report received for Chinese Patent Application No. 201980022881.8, dated Jun. 8, 2023", 14 pages (7 pages of English Translation and 7 pages of Official Copy).
"Office Action received for Great Britain Patent Application No. 1805268.8, dated Sep. 12, 2018", 4 pages.
"Office Action received for Japanese Patent Application No. 2020-551808, dated Nov. 24, 2021", 10 pages (5 pages of English Translation and 5 pages of Official Copy).
"Office Action received for Russian Patent Application No. 2020131939, dated Apr. 28, 2021", 10 pages (5 pages of English Translation and 5 pages of Official Copy).
"Office Action received for Russian Patent Application No. 2020132119, dated May 26, 2021", 2 pages (Official Copy Only).
"Reason for Refusal received for Japanese Patent Application No. 2020-551808, dated Feb. 14, 2023", 8 pages(4 pages of English Translation and 4 pages of Official Copy).
"Reason for Refusal received for Japanese Patent Application No. 2020-551825, dated Mar. 14, 2023", 32 pages (15 pages of English Translation and 17 pages of Official Copy).
"Reason for Refusal received for Japanese Patent Application No. 2020-551825, dated Sep. 21, 2021", 14 pages (7 pages of English Translation and 7 pages of Official Copy).
"Reason for Refusal received for Japanese Patent Application No. 2020-552366, dated Jul. 12, 2022", 12 pages (6 pages of English Translation and 6 pages of Official Copy).
"Search Report received for Japanese Patent Application No. 2020-552366, dated Nov. 30, 2021", 38 pages (21 pages of English Translation and 17 pages of Official Copy).
"Search report received for Russian Patent Application No. 2020131761, dated May 25, 2021", 2 pages (Official Copy Only).
Wang, Yudong, "Sensors and Applications", Mechanical Industry Press, Jul. 31, 2017, 16 pages (1 page of English Abstract and 15 pages of Official Copy).
Xu, et al., "Sensor Practical Technology", National Defense Industry Press, Dec. 31, 2016, 19 pages (1 page of English Abstract and 18 pages of Official Copy).

* cited by examiner

APPARATUS FOR GENERATING AEROSOL FROM AN AEROSOLIZABLE MEDIUM, AN ARTICLE OF AEROSOLIZABLE MEDIUM AND A METHOD OF OPERATING AN AEROSOL GENERATING APPARATUS

PRIORITY CLAIM

The present application is a National Phase entry of PCT Application No. PCT/EP2019/057784, filed Mar. 27, 2019, which claims priority from Patent Application No. 1805268.8, filed Mar. 29, 2018, each of which is hereby fully incorporated herein by reference.

TECHNICAL FIELD

The present disclosure relates to an apparatus for generating aerosol from an aerosolizable medium, an article of aerosolizable medium, a system including an apparatus for generating aerosol from an aerosolizable medium and an article of aerosolizable medium and a method of operating the apparatus for generating aerosol from an aerosolizable medium.

BACKGROUND

Articles such as cigarettes, cigars and the like burn tobacco during use to create tobacco smoke. Attempts have been made to provide alternatives to these articles by creating products that release compounds without combusting. Examples of such products are so-called "heat not burn" products, also known as tobacco heating products or tobacco heating apparatus, which release compounds by heating, but not burning, material.

SUMMARY

According to a first example, there is provided an apparatus for generating aerosol from an aerosolizable medium. The apparatus comprises: a housing; a chamber for receiving an article, the article comprising: an aerosolizable medium, and a marker arrangement comprising a first marker and a second marker spaced apart from each other by a predetermined distance; and a sensor arrangement comprising a first sensor for sensing the first marker and a second sensor for sensing the second marker. The first sensor and the second sensor are spaced from each other by approximately the same distance as the predetermined distance.

According to a second example, there is provided an article for use with the apparatus of the first example. The article comprises: an aerosolizable medium; and a marker arrangement comprising a first marker and a second marker comprising identification information, wherein the first marker and the second marker are spaced apart from each other by a predetermined distance.

According to a third example, there is provided an aerosol provision system comprising: an apparatus according to the first example; and an article according to the second example.

According to a fourth example, there is provided a method of operating an aerosol generating apparatus. The method comprises: sensing, at a first sensor of a sensor arrangement, a first indicia of an article comprising aerosolizable medium; sensing, at a second sensor of the sensor arrangement spaced a predetermined distance from the first sensor, a second indicia of the article; and operating the aerosol generating apparatus based on the first indicia and the second indicia.

Further features and advantages of the disclosure will become apparent from the following description of embodiments of the disclosure, given by way of example only, which is made with reference to the accompanying drawings.

DETAILED DESCRIPTION

As used herein, the terms "aerosolizable medium" includes materials that provide volatilized components upon heating, typically in the form of an aerosol. "Aerosolizable medium" includes any tobacco-containing material and may, for example, include one or more of tobacco, tobacco derivatives, expanded tobacco, reconstituted tobacco or tobacco substitutes. "Aerosolizable medium" also may include other, non-tobacco, products, which, depending on the product, may or may not contain nicotine. "Aerosolizable medium" may for example be in the form of a solid, a liquid, a gel or a wax or the like. "Aerosolizable medium" may for example also be a combination or a blend of materials.

The present disclosure relates to apparatus that heat an aerosolizable medium to volatilize at least one component of the aerosolizable medium, typically to form an aerosol which can be inhaled, without burning or combusting the aerosolizable medium. Such apparatus is sometimes described as a "heat-not-burn" apparatus or a "tobacco heating product" or "tobacco heating device" or similar. Similarly, there are also so-called e-cigarette devices, which typically vaporize an aerosolizable medium in the form of a liquid, which may or may not contain nicotine. The aerosolizable medium may be in the form of or provided as part of a rod, cartridge or cassette or the like which can be inserted into the apparatus. One or more aerosol generating elements for volatilizing the aerosolizable medium may be provided as a "permanent" part of the apparatus or may be provided as part of the consumable which is discarded and replaced after use. In one example, the one or more aerosol generating elements may be in the form of one or more heaters.

Figure 1:
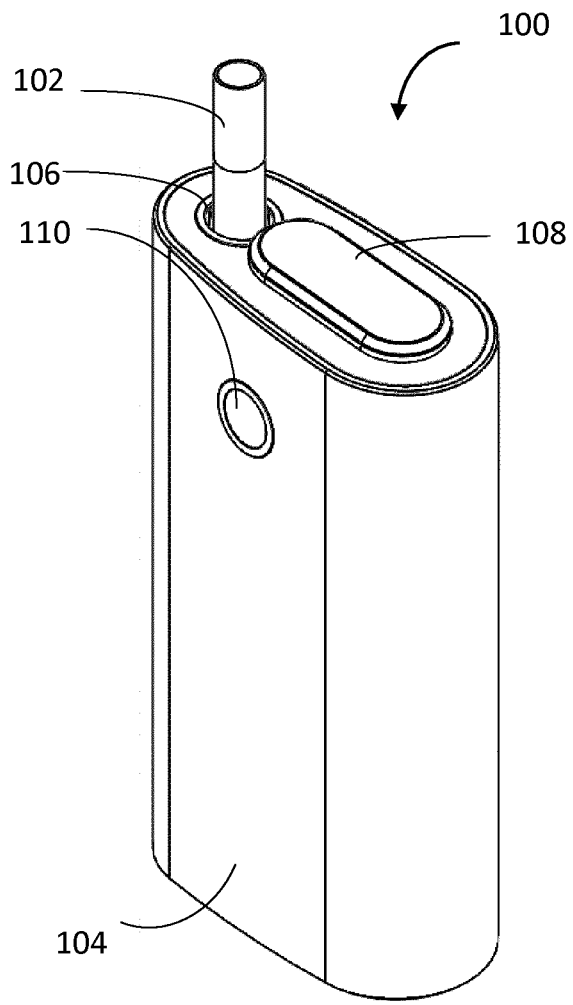
FIG. 1 shows a perspective view of an example of an apparatus for heating an article comprising aerosolizable medium.
Figure 2:
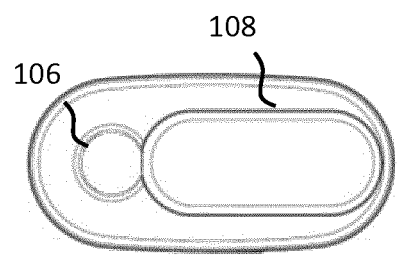
FIG. 2 shows a top view of an example of an apparatus for heating an article comprising aerosolizable medium.

FIG. 1 shows an example of an apparatus 100 for generating aerosol from an aerosolizable medium. The apparatus 100 may be an aerosol provision device. In broad outline, the apparatus 100 may be used to heat a replaceable article 102 comprising an aerosolizable medium, to generate an aerosol or other inhalable medium which is inhaled by a user of the apparatus 100. FIG. 2 shows a top view of the example of the apparatus 100 shown in FIG. 1.

The apparatus 100 comprises a housing 104. The housing 104 has an opening 106 in one end, through which the article 102 may be inserted into a heating chamber (not shown). In use, the article 102 may be fully or partially inserted into the chamber. The heating chamber may be heated by one or more heating elements (not shown). The apparatus 100 may also comprise a lid, or cap 108, to cover the opening 106 when no article 102 is in place. In FIGS. 1 and 2, the cap 108 is shown in an open configuration, however the cap 108 may move, for example by sliding, into a closed configuration. The apparatus 100 may include a user-operable control element 110, such as a button or switch, which operates the apparatus 100 when pressed.

Figure 3:
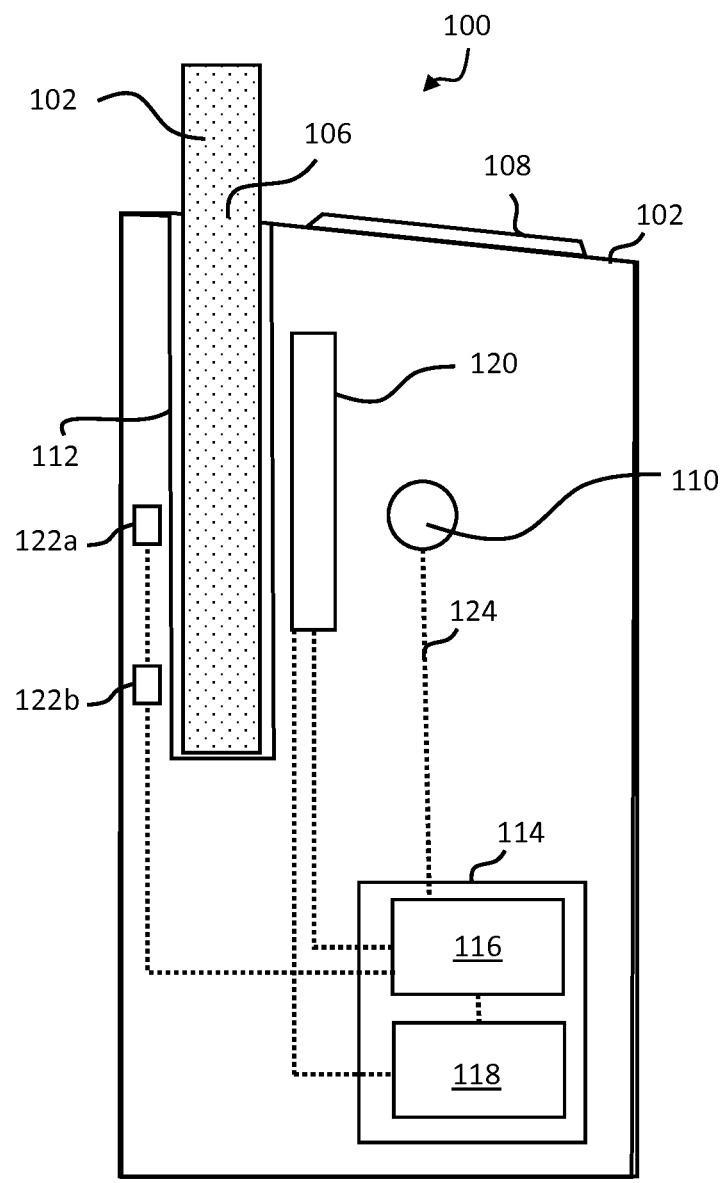
FIG. 3 shows a cross-sectional view of the example apparatus of FIG. 1.

FIG. 3 shows a cross-sectional view of an example of an apparatus 100 as shown in FIG. 1. The apparatus 100 has a receptacle, or heating chamber 112 which is configured to receive the article 102 to be heated. In one example, the heating chamber 112 is generally in the form of a hollow cylindrical tube into which an article 102 comprising aerosolizable medium is inserted for heating in use. However, different arrangements for the heating chamber 112 are possible. In the example of FIG. 3, an article 102 comprising aerosolizable medium has been inserted into the heating chamber 112. The article 102 in this example is an elongate cylindrical rod, although the article 102 may take any suitable shape. In this example, an end of the article 102 projects out of the apparatus 100 through the opening 106 of the housing 104 such that user may inhale the aerosol through the article 102 in use. The end of the article 102 projecting from the apparatus 100 may include a filter material. In other examples the article 102 is fully received within the heating chamber 112 such that it does not project out of the apparatus 100. In such a case, the user may inhale the aerosol directly from the opening 106, or via a mouthpiece which may be connected to the housing 102 around the opening 106.

The apparatus 100 comprises one or more aerosol generating elements. In one example, the aerosol generating elements are in the form of a heater arrangement 120 arranged to heat the article 102 located within the chamber 112. In one example the heater arrangement 120 comprises resistive heating elements that heat up when an electric current is applied to them. In other examples, the heater arrangement 120 may comprise a susceptor material that is heated via induction heating. In the example of the heater arrangement 120 comprising a susceptor material, the apparatus 100 also comprises one or more induction elements which generate a varying magnetic field that penetrate the heater arrangement 120. The heater arrangement may be located internally or externally of the heating chamber 112. In one example, the heater arrangement may comprise a thin film heater that is wrapped around an external surface of the heating chamber 112. For example, the heater arrangement 120 may be formed as a single heater or may be formed of a plurality of heaters aligned along the longitudinal axis of the heating chamber 112. The heating chamber 112 may be annular or tubular, or at least part-annular or part-tubular around its circumference. In one particular example, the heating chamber 112 is defined by a stainless steel support tube. The heating chamber 112 is dimensioned so that substantially the whole of the aerosolizable medium in the article 102 is located within the heating chamber 112, in use, so that substantially the whole of the aerosolizable medium may be heated. In other examples, the heater arrangement 120 may include a susceptor that is located on or in the article 102, wherein the susceptor material is heatable via a varying magnetic field generated by the apparatus 100. The heating chamber 112 may be arranged so that selected zones of the aerosolizable medium can be independently heated, for example in turn (over time) or together (simultaneously), as desired.

In some examples, the apparatus 100 includes an electronics compartment 114 that houses electrical control circuitry or controller 116 and/or a power source 118, such as a battery. In other examples, a dedicated electronics compartment may not be provided and the controller 116 and power source 118 are located generally within the apparatus 100. The electrical control circuitry or controller 116 may include a microprocessor arrangement, configured and arranged to control the heating of the aerosolizable medium as discussed further below. The apparatus 100 includes a sensor arrangement comprising a first sensor 122*a*, and a second sensor 122*b* configured to monitor for the presence of a first marker (such as a reference marker) of the article 102 and sense, read or otherwise interrogate a second marker comprising indicia or identification information of the article 102, as discussed further below.

In some examples, the controller 116 is configured to receive one or more inputs/signals from the sensor arrangement 122*a*, 122*b*. The controller 116 may also receive a signal from the control element 110 and activate the heater arrangement 120 in response to the received signal and the received inputs. Electronic elements within the apparatus 100 may be electrically connected via one or more connecting elements 124, shown depicted as dashed lines.

The power source 118 may be, for example, a battery, such as a rechargeable battery or a non-rechargeable battery. Examples of suitable batteries include, for example, a lithium-ion battery, a nickel battery (such as a nickel-cadmium battery), an alkaline battery and/or the like. The battery is electrically coupled to the one or more heaters to supply electrical power when required and under control of the controller 116 to heat the aerosolizable medium without causing the aerosolizable medium to combust. Locating the power source 118 adjacent to the heater arrangement 120 means that a physically large power source 118 may be used without causing the apparatus 100 as a whole to be unduly lengthy. As will be understood, in general a physically large power source 118 has a higher capacity (that is, the total electrical energy that can be supplied, often measured in Amp-hours or the like) and thus the battery life for the apparatus 100 can be longer.

It is sometimes desirable for the apparatus 100 to be able to operate in a power saving mode when a user is not using the apparatus 100 as this will reduce power consumption and prolong battery life. It is also desirable for the apparatus to be able to identify or recognize the particular article 102 that has been introduced into the apparatus 100, without further input from the user. For example, the apparatus 100, including, in particular, the heating control provided by the controller 116, will often be optimized for a particular arrangement of the article 102 (e.g. one or more of size, shape, particular smokable material, etc.). It would be undesirable for the apparatus 100 to be used with an aerosol medium or an article 102 having different characteristics.

In addition, if the apparatus 100 can identify or recognize the particular article 102, or at least the general type of article 102, that has been introduced into the apparatus 100, this can help eliminate or at least reduce counterfeit or other non-genuine articles 102 being used with the apparatus 100.

In one example, the sensor arrangement 122*a*, 122*b* is configured to operate in a first mode in which the sensor arrangement 122*a*, 122*b* monitors non-continuously for the presence of a first marker of the article 102, and a second mode, following the detection of said first marker, wherein the sensor arrangement 122*a*, 122*b* is configured to sense the second marker comprising identification information of the article 102. The sensor arrangement 122*a*, 122*b* comprises a first sensor 122*a* and a second sensor 122*b* that are spaced apart from each other at approximately the same distance as the first marker and the second marker.

The sensor arrangement 122*a*, 122*b* may provide one or more inputs to the controller 116, based on the sensed marker arrangement. The controller 116 may determine a parameter or characteristic of the article 102, such as whether the article 102 is a genuine article, based on the received one or more inputs. In one example, this determination is based on the characteristics of the input(s). For example, the first marker may produce a first input having a characteristic (e.g., a magnitude) which is an expected characteristic corresponding to a genuine article 102 or to a type of the aerosolizable medium of the article 102. In other examples, the determination may be made on the presence (or absence) of the input(s), e.g., if a first input is received but a second input is not, the article 102 may be determined as not genuine. The controller 116 may activate the heater arrangement 120 depending on the determined parameter of the article 102. The apparatus 100 is therefore provided with means of detecting whether the article 102 is a genuine product or not and may alter the operation of the apparatus 100 accordingly, for example, by preventing supply of power to the heater arrangement 120 if a non-genuine article is detected. Preventing use of the apparatus 100 when a non-genuine article is inserted into the apparatus 100 would reduce the likelihood of consumers having a poor experience due to the use of illicit consumables.

In some examples, the controller 116 is able to determine a parameter of the article 102 based on the received one or more inputs from the sensor arrangement 122*a*, 122*b* and tailor the heat profile provided by the heater arrangement 120 based on the determined parameter. The heater arrangement 120 of the apparatus 100 may be configured to provide a first heating profile if the identification information of the article 102 has a first characteristic (e.g., by the controller 116 controlling the supply of power) and the heater arrangement 120 is configured to provide a second heating profile if the identification information of the article 102 has a second characteristic different from the first characteristic. For example, the apparatus 100 may be able to determine whether the consumable is a solid or a non-solid consumable and adjust the heating profile accordingly. In other examples, the apparatus 100 may be able to distinguish between different blends of tobacco in the article 102 and tailor the heating profile accordingly to provide an optimized heating profile for the specific blend of tobacco that has been inserted into the apparatus 100.

FIG. 4 shows a schematic longitudinal side view of an example of an article 102 comprising aerosolizable medium for use with the apparatus 100. In some examples, the article 102 also comprises a filter arrangement (not shown) in addition to the aerosolizable medium. The article 102 also comprises a marker arrangement 126 that is configured to be sensed by the sensor arrangement 122*a*, 122*b* of the apparatus 100. The marker arrangement 126 includes a first marker 126*a* and a second marker 126*b* comprising identification information. The first marker 126*a* is configured to be sensed by the sensor arrangement 122*a*, 122*b* to indicate the presence of the article 102. The first marker 126*a* may be made up of one or more marker elements, as described below.

The second marker 126*b* may be made up of one or more marker elements and represents encoded information indicative of a parameter or characteristic of the article 102. As mentioned above, the parameter may indicate the maker of the article 102, such that the article 102 can be confirmed as genuine. In other examples, the parameter may indicate the type of aerosolizable medium in the article 102, such as whether the aerosolizable medium is in the form of a solid, liquid or gel. The parameter may also be indicative of a variant of the aerosolizable medium, such as whether the aerosolizable medium comprises Burley tobacco or Virginia tobacco. In other examples, the parameter may indicate a heating profile that should be used to heat the article 102. The parameter may indicate other characteristics of the article 102. Providing a second marker 126*b* allows the apparatus 100 to provide a tailored experience for the user based on the identification information of the article 102.

The first marker 126*a* and the second marker comprising identification information 126*b* are spaced apart from each other by a predetermined distance, S1. FIG. 4 indicates that the separation S1 is measured from the mid-point of the first marker 126*a* to the mid-point of the second marker 126*b*. However, in other examples the separation may be measured from the start of the first marker 126*a* to the start of the second marker 126*b*, the distance of any blank space between them, or any other suitable predefined dimension.

The marker arrangement 126 may comprise an optical characteristic, for example, in FIG. 4, the first marker 126*a* is a marker element in the form of a single line on the outside of the article 102 and the second marker 126*b* comprises marker elements in the form of a plurality of lines on the outside of the article 102. In FIG. 4, the lines are shown as being uniform width, but in other examples, the width of the lines may be varied. In the example of FIG. 4, the second marker 126*b* is indicative of an encoded parameter associated with the article 102. The marker 126, once read, may be compared to a look-up table (LUT) storing a correspondence between data associated with the marker 126 (e.g., a binary sequence indicated by the indicia) and a heating profile or other action associated with the apparatus. In addition, the data associated with the marker 126 may be encoded according to a secret key common to all aerosol provision apparatus from a certain manufacturer/geographic origin, and the apparatus is configured to decode the encoded data before searching for the decoded data in the LUT.

In the example of the article 102 being cylindrical, the one or more marker elements, such as lines, may extend part of the way around the perimeter or circumference of the article 102 or all of the way around the perimeter of the article 102. In some examples the sensor arrangement 122*a*, 122*b* configured to sense the marker arrangement 126 may be arranged at a specific location within the apparatus 100. For example, the sensor arrangement 122*a*, 122*b* may be arranged adjacent to one side of the chamber 112 and may have a limited detection range. Providing marker elements that extend all of the way around the perimeter of the article 102 facilitates the sensing of the marker arrangement 126 by the sensor arrangement 122*a*, 122*b*, irrespective of the particular orientation of the article 102 within the apparatus 100.

The marker arrangement 126 may be formed in a number of different ways, and be formed of a number of different materials, depending on the particular sensor arrangement 122a, 122b, of the apparatus 100 with which the article 102 is intended to be used. The marker arrangement 126 may comprise optical features such as lines, gaps or notches, surface roughness, and/or reflective material. The second marker 126b may comprise optical features such as a barcode or a QR code.

In other examples, the marker arrangement 126 comprises an electrically conductive feature and the sensor arrangement 122a, 122b may be configured to detect a change in capacitance or resistance when the article 102, including the marker arrangement 126, is inserted into the apparatus 102. Providing a non-optical sensor arrangement 122 may potentially be more robust compared with an optical sensor because it would not be affected by deposition on an optical sensor or degradation of optical sensor over the life of the apparatus 100. Non-optical sensors may be in the form of RF sensors or a hall effect sensor along with a permanent magnet or an electromagnet and a hall effect sensor. The marker arrangement 126 may be formed from an appropriate material arranged to affect the non-optical signal received by the sensors 122a, 122b.

In other examples, the marker arrangement 126 may comprise a combination of optical features and electrically conducting features, for example, the first marker 126a may comprise electrically conductive features and the second marker 126b may comprise optical features.

The marker arrangement 126 may, for example, be provided externally of the smokable article 102, internally of the article 102, or both externally and internally of the article 102. Where optical sensing is used on its own or in combination with some other sensing, such as capacitive sensing, the marker arrangement 126 is preferably provided on the outside of the article 102 so that the marker arrangement 126 is visible to the sensor arrangement 122a, 122b of the apparatus 100.

Figure 4:
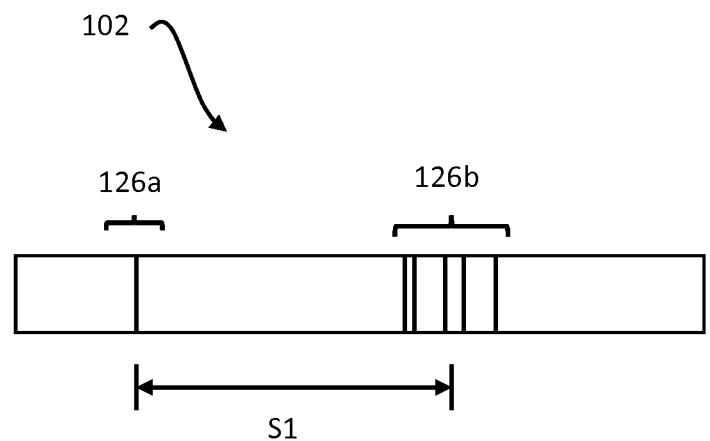
FIG. 4 shows a side view of an example of an article comprising an aerosolizable medium.
Figure 5:
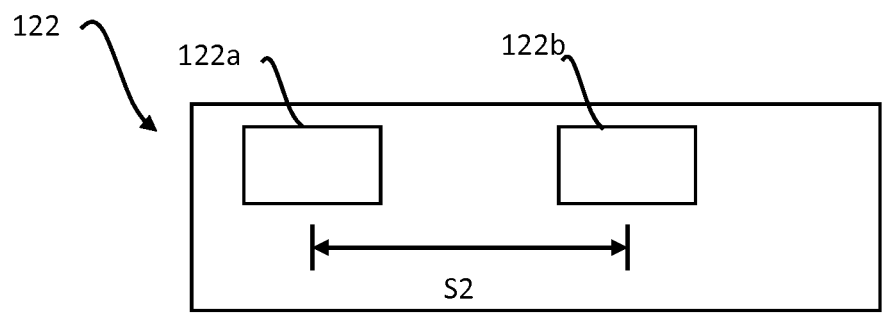
FIG. 5 shows a side view of an example of an article comprising an aerosolizable medium.

The first marker 126a and the second marker 126b are spaced apart from each other as indicated by the predetermined spacing, S1, as shown in FIG. 4. Providing a space between the first marker 126a and the second marker 126b reduces the likelihood of interference between the two regions. The sensor arrangement 122a, 122b comprises a first sensor 122a configured to sense the first marker 126a and a second sensor 122b configured to sense the second marker 126b. FIG. 5 shows an example of the sensor arrangement 122a, 122b comprising a first sensor 126a and a second sensor 126b, in which the first sensor 122a and the second sensor 122b are spaced apart by a distance S2. The first sensor 122a and the second sensor 122b are spaced from each other by approximately the same distance as the predetermined distance of the first marker 126a and the second marker, such that S1 is approximately equal to S2. The first sensor 122a and the second sensor 122b may be spaced apart from each other by any suitable distance within the apparatus 100. In one example, the first sensor 122a and the second sensor 122b are spaced from each other by less than 70 mm, more preferably less than 50 mm, more preferably less than 30 mm, more preferably less than 25, or more preferably less than 20 mm.

If the first marker 126a has been sensed by the first sensor 122a and the second marker 126b does not then line up with the second sensor 122b, then the second sensor 122b may not be able to read the identification information of the second marker 126b. As a result, matching the spacing between the first sensor 122a and the second sensor 122b and the first marker 126a and the second marker 126b provides an authenticity check of the article 102 and the apparatus 100 may be prevented from operating if the spacing does not match.

In one example, the first sensor 122a may have a first sense region in which the first sensor 122a is able to sense the first marker 126a and the second sensor 122b may have a second sense region in which the second sensor 122b is able to sense the second marker 126b. In this example, the first and second sensors 122a, 122b are spaced from each other such that a point in the first sense region and a point in the second sense region are spaced apart from each other by the predetermined distance. This arrangement provides some tolerance for the spacing of the first marker 126a and 126b. In one example, the first sense region defines a first distance along the longitudinal axis of the chamber 112 and the second sense region defines a second distance along the longitudinal axis of the chamber 112. In this example, the first and second sensors 122a, 122b are spaced from each other such by an amount between the predetermined distance minus the first and second longitudinal distances and the predetermined distance plus the first and second longitudinal distances. Again, this arrangement allows for some tolerance of the spacing of the spacing of the first marker 126a and 126b. In one example, the sense regions are defined based on the operational tolerances of the sensors. For example, the sense regions may be defined based on the field of view of an optical sensor or the range of an RFID sensor, for example, 20 mm.

This tolerance allows for the positioning of markers 126a and 126b on the consumable itself to vary between articles. For example, it may be difficult during production to ensure that the markers 126a, 126b are always in the exact same position on the consumable but the relative spacing between the markers 126a, 126b can be produced with high accuracy. By providing the sensors with a tolerance, the spacing between markers 126a, 126b can still be used for determining authenticity and/or other information of the article with a simpler production process.

In general, the sensor arrangement can be configured to determine a relative position between the first marker and a second marker. For example, the relative position may be expressed as a distance apart or a vector. The relative positioning of the first marker and the second marker can be used impart information about the article. For example, the spacing between the two markers may be used in a look up table to determine information and/or parameters relating to the consumable, such as a type of aerosolizable medium, a heating profile to use and/or whether the article is genuine. For example, relative spacing between the first and second marker may vary in increments of 0.1 mm, 0.25 mm, 0.5 mm, 1 mm or 2 mm.

In some examples the relative spacing between the markers is combined with further information read from the marker itself, such as barcode or 2-D barcode. The combination of the spacing and information read from the markers may provide a check on authenticity, with only some combinations valid. For example, a particular marker may be associated with a single relative positioning of the first and second marker. If the spacing does not substantially equal the spacing associated with the marker then the article may be determined as counterfeit.

In some examples where the sensors are operative over regions, the first sensor may indicate a position of the first marker within its sensed region as a baseline or datum for use by the second sensor. In such examples, the second sensor may determine a position of the second marker within its sensing region relative to the baseline or datum provided by the first sensor, allowing the relative position of the markers to be determined.

The first marker 126a may be configured to be sensed by the sensor arrangement 122a, 122b to determine whether the article 102 is in the vicinity of the first sensor 122a. In one example, the sensor arrangement 122a, 122b is configured to operate in a first mode when monitoring for the presence of the first marker 122a. In the first mode, the sensor arrangement 122a, 122b is not configured to detect the second marker 126b and so the apparatus may operate at a relatively low power. When the sensor arrangement 122a, 122b detects the presence of the first marker 122a of the article, it switches to a second mode in which the sensor arrangement 122a, 122b is configured to sense the second marker 122b. Restricting the sensor arrangement 122a, 122b to operate in the first mode, which consumes less power compared with the second mode, is efficient as the apparatus 100 does not have to utilize relatively high power to sense the second marker comprising identification information 122b, until the sensor arrangement 122a, 122b has already detected the first marker 122a of the article 102 is present.

In one example, in a first mode, the sensor arrangement 122a, 122b is configured to non-continuously monitor for the presence of the first marker 126a. In one example, the sensor arrangement 122a, 122b periodically monitors for the presence of the first marker 126a at regular intervals. However, in other examples, the sensor arrangement 122a, 122b monitors for the presence of the first marker 126a at irregular intervals. In one example, the sensor arrangement 122a, 122b is configured to monitor for the presence of the first marker 126a with a duty ratio of less than or equal to 10%. In one example, the sensor arrangement 122a, 122b is configured to monitor for the presence of the first marker 126a for 1 millisecond in every 10 milliseconds. Non-continuous monitoring for the presence of the first marker 126a is more energy efficient compared with continuously monitoring for the presence of the reference marker 126a as is does not require a constant source of power. It should be appreciated that the sensor arrangement 122a, 122b may be configured to begin monitoring for the presence of the first marker 126a in response to a user input, e.g., such as switching on the apparatus 100 (e.g., via a user activated button on the outside of the apparatus 100). In addition, once the first marker 126a and the second marker 126b have been sensed, the sensor arrangement 122a, 122b may be switched off for a predetermined time (i.e., no further sensing occurs for the predetermined time). These options may further reduce energy consumption.

The sensor arrangement 122a, 122b may provide a first input to the controller 116 to indicate that an article 102 comprising a first marker 126a has been detected. Upon receipt of the first input, the controller 116 may be configured to signal the sensor arrangement 122a, 122b to operate in a second mode to sense the second marker 126b. In an alternative example, the sensor arrangement 122a, 122b may be configured to sense the first marker 126a and the second marker 126b simultaneously.

The second marker 126b includes marker elements that are configured to be sensed by the sensor arrangement 122a, 122b to enable a parameter associated with the article 102 to be determined by the controller 116. In the example shown in FIG. 4, the second marker comprising identification information 126b includes four marker elements in the form of lines. The marker elements are spaced form each other at varying distances. The arrangement of the marker elements is indicative of a parameter of the article 102, as described in more detail below. For example, the arrangement of the marker elements may be indicative of the article 102 being a genuine article 102 intended for use with the apparatus 100, or it could be indicative of the heating profile to be used with this article 102. The sensor arrangement 122a, 122b is configured to provide a second input indicative of the parameter of the article 102 to the controller 116.

Where capacitive or resistive sensing is used, the marker arrangement 126 may be provided internally and/or externally of the article 102. The marker arrangement 126 may be literally "marked on" the article 102, such as by printing. Alternatively, the marker arrangement 126 may be provided in or on the article 102 by other techniques, such as being formed integrally with the article 102 during manufacture.

In certain examples, and depending on the nature of the sensing that is used to sense the marker arrangement 126, the marker arrangement 126 may be formed of an electrically conductive material. The marker arrangement 126 may be, for example, a metallic component such as aluminum or a conductive ink or ferrous or non-ferrous coating. The ink may be printed onto tipping paper of the article 102, using for example a rotogravure printing method, screen printing, ink jet printing, or any other suitable process.

In general, capacitive sensing as used herein operates by effectively sensing a change in capacitance when the article 102 is located within the apparatus 100. In effect, in an embodiment, a measure of the capacitance is obtained. If the capacitance meets one or more criteria, it may be decided that the article 102 is suitable for use with the apparatus 100, which can then proceed to operate as normal to heat the aerosolizable medium. Otherwise, if the capacitance does not meet the one or more criteria, it may be decided that the article 102 is not suitable for use with the apparatus 100, and the apparatus 100 does not function to heat the aerosolizable medium and/or may issue some warning message to the user. In general, capacitive sensing may work by providing the apparatus 100 with (at least) one electrode which in effect provides one "plate" of a capacitor, with the other "plate" of the capacitor being provided by the electrically conducting marker arrangement 126 of the apparatus 100 mentioned above. When the article 102 is inserted into the apparatus 100, a measure of the capacitance formed by the combination of the electrode of the apparatus 100 and the article 102 can be obtained, and then compared to one or more criteria to determine whether the apparatus 102 can then proceed to heat the article 102. As an alternative, the apparatus 100 may be provided with (at least) two electrodes, which in effect provide the pair of "plates" of a capacitor. When the article 102 is inserted into the apparatus 100, it is inserted between the two electrodes. As a result, the capacitance formed between the two electrodes of the apparatus 100 changes. A measure of this capacitance formed by the two electrodes of the apparatus 100 can be obtained, and then compared to one or more criteria to determine whether the apparatus 100 can then proceed to heat the article 102.

In some examples, the sensor arrangement 122a, 122b comprises at least two different sensing techniques, for example, the first sensor and the second sensor are configured to sense different properties. In one example, one sensor, such as the first sensor 122a, may comprise an optical sensor and the other sensor, such as second sensor 122b, may comprise a non-optical sensor, such as a capacitive sensor.

Figure 6:
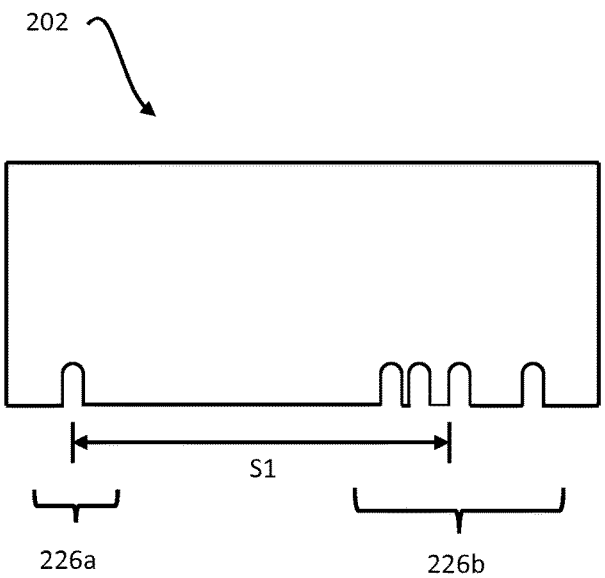
FIG. 6 shows an example of an optical sensor an example of the article of FIG. 5.

FIG. 6 shows a side view of an alternative example of an article 202 for use with an apparatus for heating aerosolizable medium. In this example, the marker arrangement 226 is in the form of a plurality of notches or holes formed in the article 202. As with the marker arrangement 126 shown in FIG. 4, the marker arrangement 226 in the example of FIG. 6 comprises a first marker 226*a* and a second marker 226*b*. In this example, the first marker 226*a* comprises a single marker element and the second marker 226*b* comprises marker elements spaced at a varying distance from each other. The first marker 226*a* and the second marker 226*b* are spaced apart by a distance S1.

Figure 7:
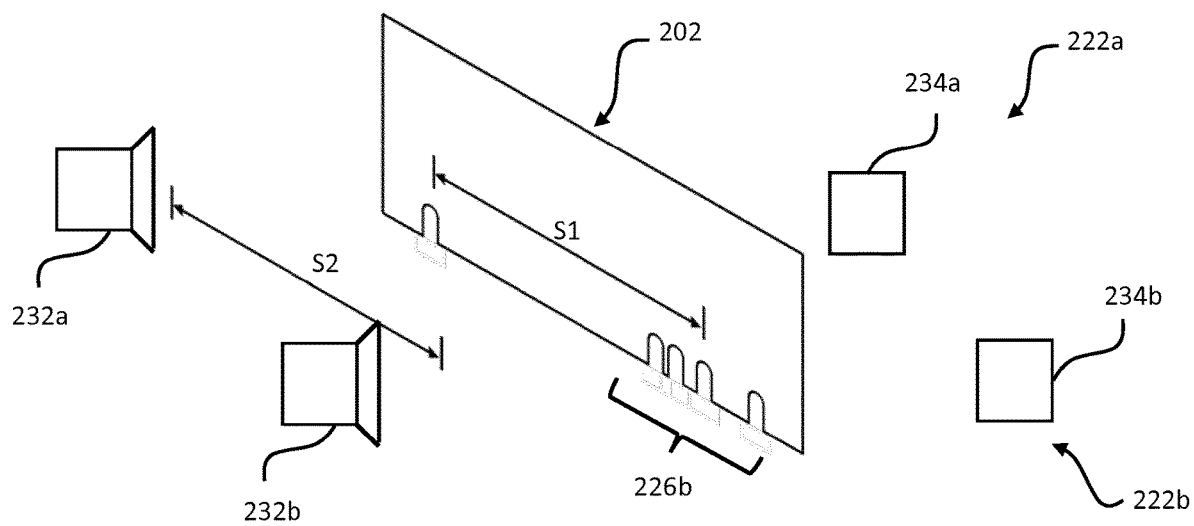
FIG. 7 shows an example of a signal generated by a sensor arrangement.

FIG. 7 shows an illustrative example of an optical sensor arrangement 222*a*, 222*b*. In this example, the sensor arrangement 222*a*, 222*b* comprises a first sensor 222*a* in the form of a first light source 232*a*, such as an LED, and first light receiver 234*a*, such as light sensor, and a second sensor 222*b* in the form of a second light source 232*b* and a second light receiver 234*b*. The light receivers 234*a*, 234*b* are configured to receive light from the light sources 232*a*, 232*b*. In use, as the article 202 is located next to the sensors arrangement 222*a*, 222*b* in between the light sources 232*a*, 232*b* and the receivers 234*a*, 234*b*, the article 202 blocks the light and prevents it from being received at the receivers 234*a*, 234*b*. In other examples, the article 202 reduces the amount of light being received at the receivers 234*a*, 234*b*, rather than blocking it. However, light is not blocked in the location of the marker elements in the form of a notches. Therefore, the quantity of light received at the receivers 234*a*, 234*b* will vary across the length of the article 202 depending on whether a notch is within the light path between the light sources 232*a* and the receivers 234 or not. In this example, the first sensor 222*a* of the sensor arrangement is spaced from the second sensor of the sensor arrangement 222*b* by a distance S2.

Figure 8:
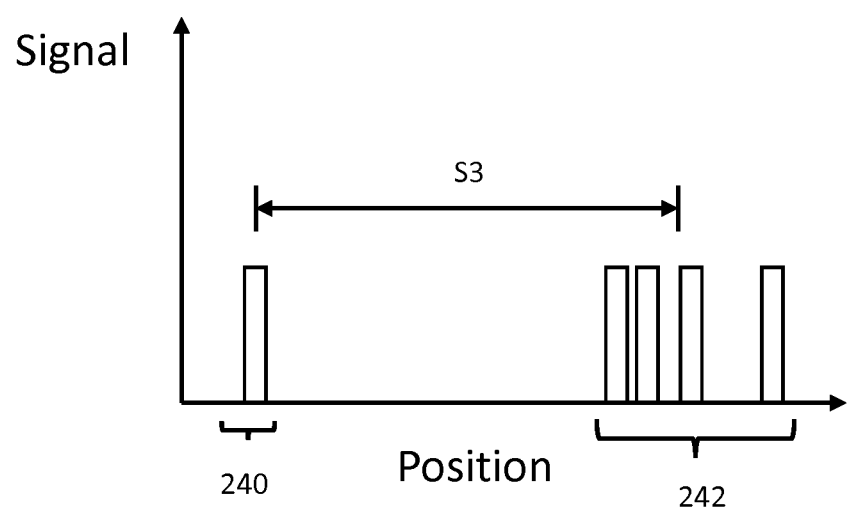
FIG. 8 shows an example of a signal generated by a sensor arrangement.
Figure 9:
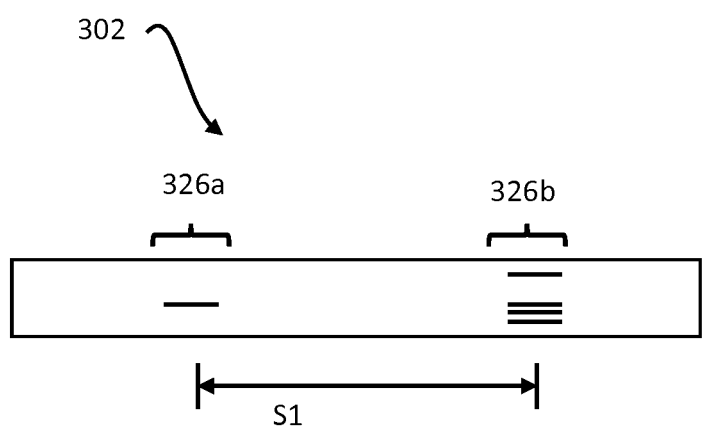
FIG. 9 shows a side view of an example of an article comprising an aerosolizable medium.

FIG. 8 shows an example of a signal generated by the sensor arrangement 222*a*, 222*b*. In this example, a first signal 240 is a representation of light received by the first light sensor 234*a* from the first light source 232*a* and the second signal 242 is a representation of light received by the second light sensor 234*a* from the second light source 232*a*. The position of the peaks of the first signal 240 is equivalent to the positioning of the first marker 226*a* on the article 202 and the position of the peaks of the second signal 242 is indicative of the arrangement of the second marker 226*b*. As shown in FIG. 8, the distance between the center point of the peaks of the first signal 240 and the peaks of the second signal 242 is S3, which is substantially equal to S1 and S2. If the distance S2 between the first sensor 222*a* and the second sensor 222*b* is not substantially equal to the distance S1 between the first marker 226*a* and the second marker 226*b*, then part or all of one of the signals 240, 242 will be missing, which will be indicative of the article 202 not being genuine.

In one example, in a first mode, the sensor arrangement 222*a*, 222*b* is configured to non-continuously monitor for the presence of the first marker 226*a* so power is not supplied to the light source 232*b* and light receiver 234*b* during the first mode. The first signal 240 shown in FIG. 8 may be provided to the controller 216 as a first input, which determines whether the position and size of the first marker 226*a* indicates that the article 202 is genuine or not, for example, by using a look-up table. If the controller 216 determines that the first marker 226*a* is indicative of the article 202 being genuine, then the sensor arrangement 222*a*, 222*b* will switch to a second mode wherein power is supplied to the to the light source 232*b* and light receiver 234*b* to enable the second sensor 222*b* to sense the second marker 226*b*. The second signal 242 shown in FIG. 8 may be provided to the controller 216 as a second input. The controller 116 determines identification information of the article 202, for example, by using a look-up table. The second input is indicative of a parameter of the article 202 and so enables the controller 116 to determine the parameter of the article 202.

In the example shown in FIG. 7, the sensor arrangement 222*a*, 222*b* comprises two light sources 232*a*, 232*b* and two light receivers 234*a*, 234*b*. However, in other examples, the optical sensor may comprise an array of light sources and an array of light sensors. In the example of the marker arrangement 226 comprising a reflective material, the light source 232 and the light receiver 234 may be formed in a single element and light will be reflected back to the light source/receiver to indicate the position of the marker element.

In other examples, the sensor arrangement 122*a*, 122*b*, 222*a*, 222*b* is configured to sense the marker arrangement 126, 226 by measuring the reflection or surface roughness from the surface of the article 102, 202. In other examples, the sensor arrangement 122*a*, 122*b*, 222*a*, 222*b* may be configured to sense and read the marker comprising identification information 126*b* in the form of a barcode or QR code. In other examples, the sensor arrangement 122*a*, 122*b*, 222*a*, 222*b* may be configured to sense visible or invisible fluorescent material.

The controller 116 may comprise pre-programmed information, such as a look-up table, that includes details of the various possible arrangements of the second marker 126*b*, 226*b* and what parameter is associated with each arrangement. Therefore, the controller 116 is able to determine the parameter associated with the article 102, 202.

The controller 116 may be arranged so that it will only heat an article 102, 202 that it recognizes, and will not operate in conjunction with an article 102, 202 that it does not recognize. The apparatus 100 may be arranged so that it provides some indication to the user that the article 102, 202 has not been recognized. This indication may be visual (for example a warning light, which may for example flash or be illuminated continuously for a period of time) and/or audible (for example a warning "beep" or the like). Alternatively or additionally, the apparatus 100 may be arranged so that, for example, it follows a first heating pattern when it recognizes a first type of article 102, 202 and follows a second, different heating pattern when it recognizes a second type of article 102, 202 (and optionally may provide yet further heating patterns for other types of article 102, 202). The heating patterns may differ in a number of ways, for example the rate of delivery of heat to the aerosolizable medium, the timing of various heating cycles, which part(s) of the aerosolizable medium are heated first, etc., etc. This enables the same apparatus 100 to be used with different basic types of article 102, 202 with minimal interaction required of the user.

FIG. 9 shows a schematic longitudinal side view of another example of an article 302 comprising aerosolizable medium for use with the apparatus 100. As with the article 102 shown in FIG. 4, the article 302 comprises a marker arrangement 326*a*, 326*b* in the form of optical lines. In this example, the lines extend substantially along the longitudinal axis of the article 302, rather than substantially perpendicular to the longitudinal axis, as is shown in the example of the article 102 in FIG. 4.

As with the articles 102, 202 shown in the examples of FIGS. 4 and 6, the marker arrangement 326 is split into a first marker 326*a* (such as a reference marker) and a second marker 326*b*. The first marker 326*a* and the second marker 326*b* are spaced by a distance S1.

In the example shown in FIG. 9, the second marker 326*b* includes four marker elements in the form of lines with a varied spacing therebetween. In one example, the spacing of the marker elements may be such as to create a defined start of the marker element and a defined end of the marker elements. As the article 302 could be inserted into the apparatus 100 in any orientation, the article 302 would need to make a full or partial rotation for all of the marker elements to be read by the one or more sensors 322a, 322b to determine the spacing of the marker elements.

In some examples, the article 102, 202, 302 may have a location feature that enables the consumable to be inserted into the apparatus 100 with a defined orientation. For example, the article may comprise a protrusion or a cut-out feature that corresponds to a shape in the opening 106 of the apparatus 100. Thus, in some implementations, the article 102, 202, 302 may only be inserted into the apparatus 100 in a single orientation. In the example of the article 102, 202, 302 being subsequently rotated, the starting position would be known and as such there would be no requirement for the article 102, 202, 302 to be rotated by at least 360 degrees. In other examples, the article 102, 202, 302 may have a predefined finger holds or orientation to align or feed into a device (ensuring the consumable is inserted in a predefined manner.

In some examples the one or more sensors 122a, 122b may be arranged at a specific location within the apparatus 100. For example, the sensor arrangement 122a, 122b may be arranged within the chamber 112 and may have a limited detection range. Similarly, the marker arrangement 126 may be arranged at a specific location on, or within the article 102, 202, 302, and may occupy a certain area or volume of the article 102. To ensure that the marker arrangement 126 is detected when a user inserts the article 102 into the receptacle, it is desirable for the apparatus 100 to be able to restrict the orientation of the article 102 to a single orientation when engaged with the chamber 112. This may ensure that the marker arrangement 126 is correctly aligned with the sensor arrangement 122a, 122b, so that it can be detected.

Figure 10:
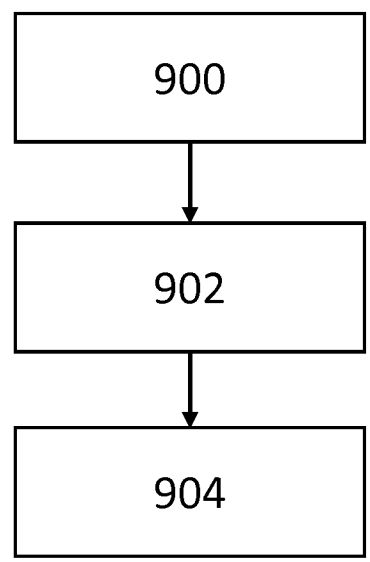
FIG. 10 shows an example of a flow chart of a method for determining a parameter associated with an article.

FIG. 10 shows an example of a flow diagram of an operation an aerosol generating apparatus 100. At step 900, the apparatus 100 senses, at a first sensor 122a of a sensor arrangement, a first indicia 126a of an article 102 comprising aerosolizable medium. At step 902, the apparatus 100 senses, at a second sensor 122*b* of the sensor arrangement, a second indicia of the article 100. At step 904 the apparatus 100 operates the aerosol generating apparatus based on the first indicia and the second indicia.

In some examples, the controller 116 controls the operation of the one or more heaters 120 based on the parameter of said article, for example, if the controller determines that a counterfeit article has been inserted into the apparatus 100, then the heaters are not activated. Alternatively, the controller 116 may determine the type of aerosolizable medium within the article, such as solid, liquid or gel and tailor the heating profile accordingly.

In some examples, multiple first and second sensors may be provided spaced at different predetermined distances. For example, a first first sensor and a first second sensor may be spaced at one predetermined distance, and a second first sensor and second second sensor may be spaced at a different predetermined distance. These different predetermined distances may correspond to different articles 102 which may have markers spaced at different predetermined distances. Accordingly, the controller 116 may be configured to sense different articles 102 based upon which of the sensor groups detects input(s). This enables the controller 116 to distinguish between articles 102 based solely or additionally on which sensors detect an input. It should also be appreciated that sensors of one 'group' may be used to define further groups of sensors—that is the first first sensor and the second second sensor may define their own group, and an input detected by these sensors signifies a different article to an input sensed by the first group or the second group.

The article 102, 202, 302 may comprise one or more flavorants. As used herein, the terms "flavor" and "flavorant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, *cassia*, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may comprise natural or nature-identical aroma chemicals. They may be in any suitable form, for example, oil, liquid, powder, or gel.

The above embodiments are to be understood as illustrative examples of the disclosure. Further embodiments of the disclosure are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. An apparatus for generating aerosol from an aerosolizable medium, the apparatus comprising:

a housing;

a chamber for receiving an article, the article comprising:

an aerosolizable medium, and a marker arrangement comprising a first marker and a second marker spaced apart from each other by a predetermined distance; and a sensor arrangement comprising a first sensor for sensing the first marker and a second sensor for sensing the second marker, wherein:

the first sensor and the second sensor are spaced from each other by approximately a same distance as the predetermined distance;

the first sensor has a first sense region in which the first sensor is able to sense the first marker;

the second sensor has a second sense region in which the second sensor is able to sense the second marker; and the first sensor and the second sensor sensors are spaced from each other such that a point in the first sense region and a point in the second sense region are spaced apart from each other by the predetermined distance.

2. The apparatus according to claim 1, wherein the sensor arrangement is configured to determine a relative positioning of the first marker and the second marker.

3. The apparatus according to claim 1, wherein the chamber defines a longitudinal axis and the first sensor and the second sensor are disposed along a direction substantially parallel to the longitudinal axis of the chamber.

4. The apparatus according to claim 1, wherein:
the first sense region defines a first distance along a longitudinal direction of the chamber;
the second sense region defines a second distance along the longitudinal direction of the chamber, and
the first sensor and the second sensor are spaced from each other such by an amount between the predetermined distance minus the first distance and the second distance and the predetermined distance plus the first distance and the second distance.

5. The apparatus according to claim 1, further comprising one or more aerosol generating elements configured to be activated based on a sensed identification information of the article.

6. The apparatus according to claim 5, wherein the one or more aerosol generating elements comprises a heater arrangement.

7. The apparatus according to claim 6, wherein the heater arrangement is configured to provide a first heating profile if the identification information has a first characteristic and the heater arrangement is configured to provide a second heating profile if the identification information has a second characteristic different from the first characteristic.

8. The apparatus according to claim 1, wherein the sensor arrangement comprises an optical sensor.

9. The apparatus according to claim 1, wherein the sensor arrangement comprises a capacitive sensor.

10. The apparatus according to claim 1, wherein the first sensor and the second sensor are different types of sensors.

11. The apparatus according to claim 1, wherein the predetermined distance is less than 70 mm.

12. The apparatus according to claim 1, wherein the marker arrangement comprises optical features.

13. The apparatus according to claim 1, wherein the marker arrangement comprises electrically conductive features.

14. The apparatus according to claim 1, wherein the article defines an insertion axis and the marker arrangement is disposed along a direction substantially parallel to the insertion axis.

15. The apparatus according to claim 1, wherein the marker arrangement is disposed around at least a portion of a perimeter of the article.

16. The apparatus according to claim 1, wherein the identification information of the article indicates that the article comprises at least one of a solid, a liquid, or a gel.

17. An aerosol provision system comprising:
the apparatus according to claim 1; and
an article for use with the apparatus, the article comprising:
an aerosolizable medium; and
a marker arrangement comprising a first marker and a second marker comprising identification information, wherein the first marker and the second marker are spaced apart from each other by a predetermined distance.

18. A method of operating an aerosol generating apparatus according to claim 1, the method comprising:
sensing, at a first sensor of a sensor arrangement, a first indicia of an article comprising an aerosolizable medium;
sensing, at a second sensor of the sensor arrangement spaced a predetermined distance from the first sensor, a second indicia of the article;
determining a distance between the first indicia and the second indicia; and
operating the aerosol generating apparatus based at least the distance between the first indicia and the second indicia.

* * * * *